United States Patent [19]

Weinberger

[11] Plant 4,903

[45] Oct. 26, 1982

[54] PEACH TREE

[75] Inventor: John H. Weinberger, Fresno, Calif.

[73] Assignee: Superior Farming Company, Bakersfield, Calif.

[21] Appl. No.: 253,161

[22] Filed: Apr. 10, 1981

[51] Int. Cl.[3] ..... A01H 5/00

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is of medium size and vigor, upright-spreading, dense, and round-topped; foliated with medium size, ovate, lanceolate and acutely pointed leaves having a crenate margin, small, green, irregularly opposite, globose glands, and a petiole medium in length and thickness; flowers from plump, appressed, pubescent flower buds of medium size and length; the flowers, of medium season, being large and pink; and the tree is a regular and productive bearer of uniform, medium size, symmetrical, globose, freestone fruit having yellow skin substantially overspread and flushed with medium light red, yellow flesh, and a medium size, elliptical, light buff stone.

1 Drawing Figure

BACKGROUND OF THE VARIETY

1. Field of the Invention

In the conduct of an extensive plant breeding program—on behalf of a commercial farming company, and in such company's experimental orchard located near Fresno, Fresno County, Calif.—I have originated a substantial number of new and distinct varieties of fruit trees, and which include the present variety of peach tree.

2. Classification of the Variety

The present variety of peach tree is embraced by Class 43, Plants, of the U.S. Patent Office Manual of Classification.

3. Prior Varieties

Among existing varieties of peach trees which are known to me, and mentioned herein, are the Springcrest and Flavorcrest (both unpatented).

ORIGIN OF THE VARIETY

The present variety of peach tree was originated by me as a cross between the Flavorcrest (as the seed parent) and Springcrest (as the pollen parent). A number of seedlings of such cross were grown to fruition, in the aforesaid experimental orchard, under careful and continuing observation by me; the present variety being a selection from such seedlings which evidenced commercial promise.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of peach tree is, characteristically, of medium size and vigor, upright-spreading, dense, and round-topped; foliated with medium size, ovate, lanceolate and acutely pointed leaves having a crenate margin, small, green, irregularly opposite, globose glands, and a petiole medium in length and thickness; flowers from plump, appressed, pubescent flower buds of medium size and length; the flowers, of medium season, being large and pink; and the tree is a regular and productive bearer of uniform, medium size, symmetrical, globose, freestone fruit having yellow skin substantially overspread and flushed with medium light red, yellow flesh, and a medium size, elliptical, light buff stone.

The present variety of peach tree is further characterized, in comparison with the Springcrest (the pollen parent), by fruit which bears general resemblance in size, shape, and appearance, but ripens about a week later.

The present variety of peach tree is further characterized, in comparison with Flavorcrest (the seed parent), by fruit which is smaller in size, smoother and more rounded in shape, with less pubescence, and ripens about three weeks earlier.

By reason of the ripening period of its fruit relative to that of the Springcrest and Flavorcrest, the present variety of peach tree is in harvest and desirably provides Sprincrest-type fruit to the market in the harvest-period gap between said other varieties; the fruit of the present variety being additionally characterized by red external or skin color which does not become too dark under California growing conditions.

BRIEF DESCRIPTION OF THE DRAWING

The drawing is an illustration, by photographic reproduction in color, of a twig with leaves, separate fruit, and a separate stone; one such fruit being half cut away to expose the flesh and stone; the latter remaining in place.

DESCRIPTION OF THE VARIETY

The botanical details of this new and distinct variety of peach tree—with color definitions (except those in common color terms) referenced to Plochere Color System (in book form)—are as follows:

Tree:

*Size.*—Medium.
*Vigor.*—Medium.
*Growth.*—Upright-spreading.
*Density.*—Dense.
*Form.*—Round-topped.

*Production.*—Productive.
*Bearing.*—Regular bearer.

Trunk:
*Size.*—Medium.
*Texture.*—Medium.

Branches:
*Size.*—Medium.
*Texture.*—Medium.
*Color.*—New wood: green. Dull. Mature wood: brown.

Leaves:
*Size.*—Medium. Average length — 16.8 cm. Average width — 3.8 cm.
*Form.*—Ovate. Lanceolate. Acutely pointed.
*Thickness.*—Medium.
*Color.*—Medium green.
*Texture.*—Smooth.
*Margin.*—Crenate.
*Petiole.*—Medium length. Medium thickness.
*Glands.*—Average number — 3. Opposite irregularly. Small. Globose. Green. Positioned distal on petiole and on base of blade.
*Stipules.*—Shed as leaves mature.

Flower buds:
*Size.*—Medium.
*Length.*—Medium.
*Form.*—Plump. Appressed. Pubescent.

Flowers:
*Date of full bloom.*—Mar. 2nd, 1980. Medium, as compared with other varieties.
*Size.*—Large.
*Color.*—Pink.

Fruit:
*Maturity when described.*—Firm ripe — June 10th, 1980.
*Date of first picking.*—June 5th, 1980.
*Date of last picking.*—June 14th, 1980.
*Size.*—Uniform. Medium. Average diameter axially — 65 mm. Average transversely in suture plane — 66 mm.
*Form.*—Symmetrical. Globose.
*Suture.*—An inconspicuous line extending over entire circumference. Slight indentation beyond pistil point.
*Ventral surface.*—Rounded. Lipped throughout both sides.
*Lips.*—Equal.
*Cavity.*—Rounded. Elongated in suture plane with suture showing on both sides. Average depth — 10 mm. Average breadth — 17 mm. Markings — none.
*Base.*—Truncate.
*Apex.*—Rounded.
*Pistil point.*—Oblique.

Skin:
*Thickness.*—Medium.
*Texture.*—Medium.
*Tenacity.*—Slightly tenacious to flesh.

*Tendency to crack.*—None in dry season.
*Color.*—Ground color — yellow (Plate 7 — No. 147 — Nasturtium) blushed with medium light red (Plate 17 — No. 387 — Cerise Pink).
*Down.*—Scant. Short. Does not roll up when rubbed.

Flesh:
*Color.*—Yellow (Plate 7 — No. 148 — Golden Rapture). Surface of pit cavity — yellow (Plate 7 — No. 148 — Golden Rapture).
*Amygdalin.*—Wanting.
*Juice.*—Abundant.
*Texture.*—Medium. Melting.
*Fibers.*—Few. Fine. Tender.
*Ripens.*—Evenly.
*Flavor.*—Acid. Delicate.
*Aroma.*—Distinct.
*Eating quality.*—Best.

Stone:
*Type.*—Free.
*Fibers.*—Short. Retains short fiber-like threads along ridges.
*Size.*—Medium. Average length — 33 mm. Average breadth — 25 mm. Average thickness — 18 mm.
*Form.*—Elliptical.
*Base.*—Straight.
*Hilum.*—Oval.
*Apex.*—Acuminate.
*Sides.*—Equal.
*Surface.*—Irregularly furrowed toward apex. Ridged toward apex. Pitted from base to above center.
*Ridges.*—Rounded.
*Pits.*—Some circular, some elongated.
*Ventral edge.*—Thick, with wing throughout.
*Dorsal edge.*—Narrow, with shallow groove throughout.
*Color.*—Light buff (Plate 7 — No. 166 — Orange cream).
*Tendency to split.*—Slight in dry season.

Use: Market.
Keeping quality: Good.
Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, particularly characterized by the bearing of uniform, medium size, symmetrical, globose, freestone fruit having yellow skin blushed with medium light red, and yellow flesh; the fruit ripening about a week later than Springcrest, and about three weeks earlier than Flavorcrest.

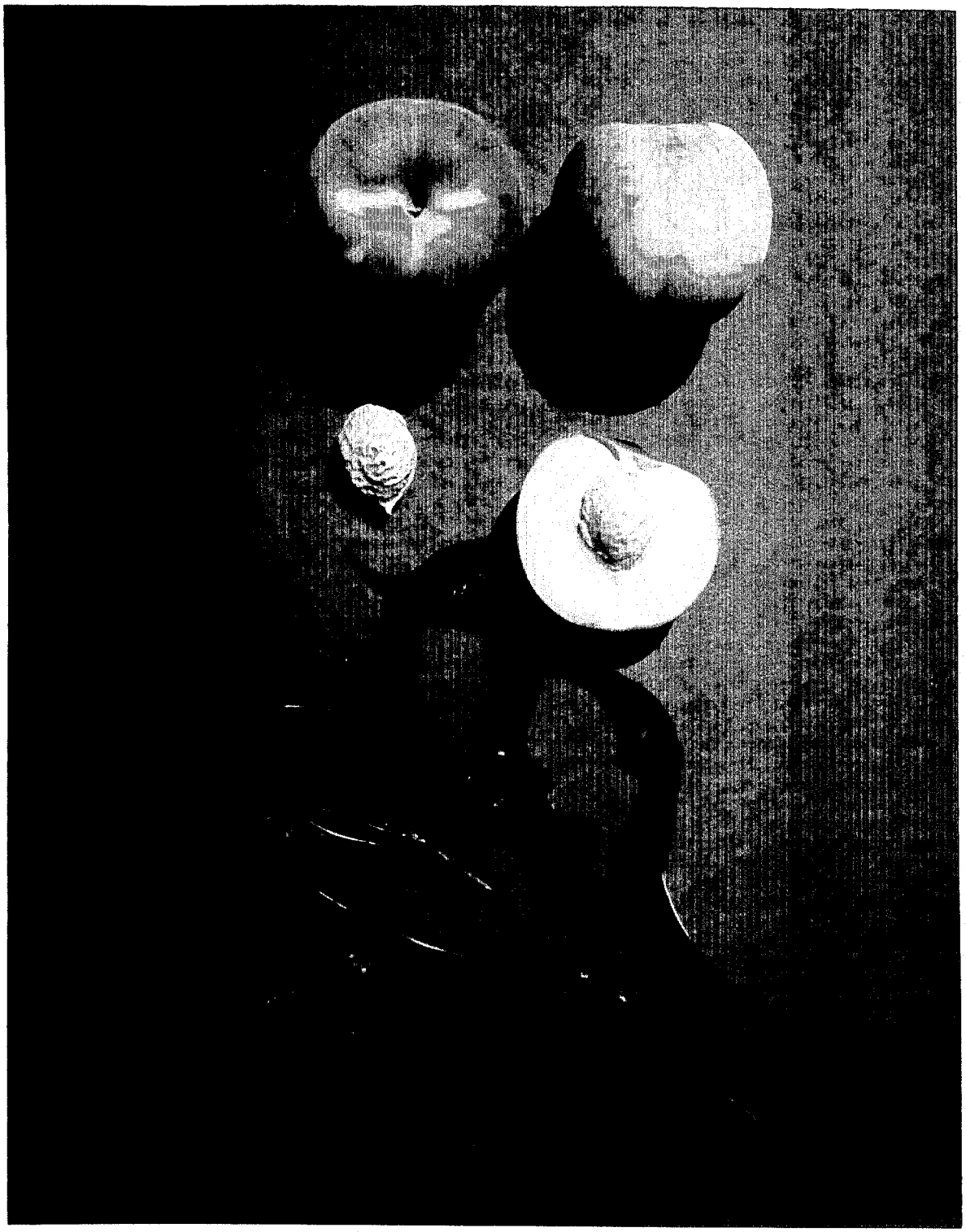

* * * * *